(12) United States Patent
Chauveau et al.

(10) Patent No.: US 7,338,161 B2
(45) Date of Patent: Mar. 4, 2008

(54) OPTICAL ACCOMMODATIVE COMPENSATION SYSTEM

(75) Inventors: Jean-Pierre Chauveau, Paris (FR); Gilles Le Saux, Paris (FR); Bruno Decreton, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 0 days.

(21) Appl. No.: 10/569,383

(22) PCT Filed: Aug. 11, 2004

(86) PCT No.: PCT/FR2004/002120

§ 371 (c)(1),
(2), (4) Date: Jul. 24, 2006

(87) PCT Pub. No.: WO2005/022241

PCT Pub. Date: Mar. 10, 2005

(65) Prior Publication Data

US 2007/0030444 A1    Feb. 8, 2007

(30) Foreign Application Priority Data

Aug. 26, 2003  (FR) .................................. 03 10171

(51) Int. Cl.
*G02C 7/06* (2006.01)
(52) U.S. Cl. ...................... 351/168; 351/159; 351/161; 351/164; 351/172
(58) Field of Classification Search ................ 351/151, 351/164, 168–172
See application file for complete search history.

(56) References Cited

U.S. PATENT DOCUMENTS

| 2,164,801 A | 7/1939 | Dittmer |
| 3,027,803 A * | 4/1962 | Filderman ............... 351/160 R |
| 2006/0058874 A1 * | 3/2006 | Peli ........................... 623/6.28 |

* cited by examiner

*Primary Examiner*—Scott J. Sugarman
*Assistant Examiner*—Darryl J. Collins
(74) *Attorney, Agent, or Firm*—Young & Thompson (57) ABSTRACT

The optical system presents accommodation compensation, the system including in combination two multifocal lenses, one of them being an aperture lens and the other a field lens.

9 Claims, 4 Drawing Sheets

OPTICAL ACCOMMODATIVE COMPENSATION SYSTEM

TECHNICAL FIELD TO WHICH THE INVENTION RELATES

The present invention relates in general to compensating or correcting vision disorders, and more particularly to cases in which the accommodation function of the eye is deficient. Concretely, the invention relates to an optical system implemented for compensating this deficiency, and to visual equipment incorporating the system.

Still more specifically, but not exclusively, the invention relates to the field of implanting artificial intraocular lenses, in which case it relates to an optical system for correcting the aphakic eye.

TECHNOLOGICAL BACKGROUND

In general, an optical system for compensating or correcting vision can make use of two main types of lens.

An aperture lens is designed to exercise the optical function that gives it its correcting or compensating power either in or against the eye. It is typically an intraocular lens or a corneal contact lens. The optical function exerted on the eye by such an aperture lens depends on the aperture of the pupil, but is independent of the direction in which the eye is looking.

In contrast, a field lens is designed to perform its optical function at a distance from the eye. It is typically constituted by a lens in a pair of spectacles mounted in a frame placed on the nose of the wearer. It may also be constituted by a monocle. The optical function performed on the eye by such a field lens depends on the direction in which the eye is looking, but is independent of the aperture of the pupil.

These two types of lens are generally used as alternatives, i.e. in optical correction systems the lenses used belong to one or other of the two above-mentioned types, to the exclusion of lenses of the other type. More rarely, in special cases that are mentioned below, it can happen that both types of lens are combined within a single correction optical system. The present invention relates specifically to such a hybrid system and proposes the use thereof in the following context.

Amongst the various vision disorders that can affect the eye, the present invention relates more particularly to partial or complete loss of accommodation.

Accommodation is the process whereby the eye can focus on objects that are closer or further away, thus enabling objects to be seen in succession and in focus even though they are situated at different distances away, referred to clinically as observation distances or working distances. Conventionally, three observation zones are distinguished: the far vision zone corresponding to observation distances of about 5 meters (m), the intermediate vision zone corresponding to observation distances of about 1 m to about 1.5 m, and the near vision zone corresponding to observation distances of abut 30 centimeters (cm) to 40 cm. Physiologically, the phenomenon of accommodation is based on controlled deformation of the natural lens, leading to a change in the curvature of its surfaces under the effect of the zonule being put under tension or relaxed. When a subject goes from far vision to near vision, the image of the retina goes out of focus and the macular diffusion circle triggers a reflex contraction of the circular portion of the ciliary muscle. This contraction of the ciliary muscle relaxes the tensions of the zonule and allows the lens to become rounder, increasing its sagittal diameter and decreasing its frontal diameter, thereby increasing its spherical power. Conversely, when the eye focuses on a distant point or a point at infinity, the ciliary muscle is relaxed and since the zonule is under tension, the lens flattens.

The accommodation function of the eye can be affected in two main ways.

Firstly in almost systematic manner, during the lifetime of an individual, capacity for visual accommodation decreases, such that most people in their forties or older require different spherical power corrections for near vision and far vision. That is presbyopia. It is recalled at this point that presbyopia is not a kind of ametropia, but is additional to the preexisting ametropia of the patient, if any.

In order to mitigate accommodation deficiency, a person suffering from presbyopia must use one or more types of visual equipment serving not only to correct any ametropia and/or astigmatism, but also to compensate for said accommodation deficiency. Several solutions are available. It is possible to wear either a plurality of pairs of field-lens spectacles, each having a respective single focus, and with the pair of spectacles that is selected being adapted to the observation distance of interest at any given time, or a single pair of field lens spectacles can be used that are multifocal, and preferably progressive, or indeed it is possible to use a pair of contact lenses, i.e. aperture lenses, that are multifocal.

It is known that a multifocal lens possesses a plurality of spherical powers or focuses that differ depending on the zone of the lens that is taken into consideration. Thus, the field lenses of multifocal spectacles have power that varies as a function of the direction in which the eye is looking, with far vision being in the top of the lens and near vision at the bottom. In multifocal contact lenses, the multiplicity of focuses provides a focus depth or caustic that gives the overall visual system of the patient a capacity for pseudo-accommodation. A plurality of images are formed simultaneously on the retina coming from the various far vision, near vision, and optional intermediate vision zones that present different powers. Adaptation with this type of lens is based on the brain discriminating between these multiple images.

When such multifocal lenses have been selected, be they contact lenses or the lenses of spectacles, they must in all circumstances present addition that corresponds to the full requirements or the wearer, since they must mitigate the wearer's lack of accommodation on their own. As a result, if the lack of accommodation is marked, the addition of the accommodation-correcting lens needs to be strong. Unfortunately, investigation work carried out by the Applicant has shown that the addition strength of a lens needs to be considered as a factor contributing to it being rejected by wearers or at least acting as a brake to wearers adapting thereto. This seems to be particularly true for contact lenses.

A patient presenting presbyopia can also envisage wearing contact lenses (i.e. aperture lenses) having a single focus for correcting ametropia in far vision or in near vision, in combination, for the remainder of the observation range, with a pair of spectacles presenting (field) lenses having a single focus. That produces a hybrid system combining both types of lens, field lenses and aperture lenses. Nevertheless, it should be observed that both types of lens then have respective single focuses.

In addition to the physiological disorder of presbyopia, it can happen that the eye suffers from refraction disorders or even from more severe pathologies, leading the ophthalmologist to have recourse to surgery in order to implant an intraocular lens, possibly after removing the patient's natural lens from the eye (where an eye deprived of its natural lens in this way is said to be aphakic). In particular, replacing the natural lens by an intraocular implant constituting an artificial aperture lens has become an operation that is commonplace for cataract surgery and for high degrees of ametropia (in particular of myopia). The drawback is that the aphakic eye loses all natural accommodation power. It is then necessary to give the patient after the operation some kind of accommodation capacity or at least to provide a palliative (the term "compensation" is used). For this purpose, several solutions have been proposed as alternatives.

A first solution consists in implanting a rigid multifocal lens (aperture lens) that does not provide the visual system of the patient with any capacity for accommodation, and to make provision for simultaneously wearing external visual equipment such as a pair of spectacles (field lenses). The surgeon and the patient then need to make a choice between near vision and far vision when determining the power to be given of the intraocular implant. For the remainder of the range of vision, additional correction is essential so the patient must have one or more pairs of single-focus or multiple-focus spectacles. For example, if the patient receives a single focus intraocular implant lens designed for far vision, then that patient does not have the slightest accommodation for intermediate vision or near vision. In order to be able to assess this portion of the visual range, the patient must either wear at least two different pairs of spectacles having single-focus lenses, or a pair of glasses having lenses that are multifocal and preferably progressive. Under such circumstances, which can be considered as being the most practical for the wearer, the multifocal field lenses of the pair of spectacles must present strong addition since they must be capable on their own of mitigating the total loss of the patient's natural accommodation capacity. Unfortunately, studies carried out by the Applicant have led to the conclusion that in combination with the upheaval constituted by the surgery and the artificial implant itself, particularly in patients who are quite old, wearers find it difficult to tolerate high power progressive lenses.

A second solution consists in implanting an intraocular lens presenting accommodation, that is capable of deforming or moving under the action of the ciliary muscle in order to adapt its focus to the visual needs of the patient having the implant, thereby restoring the natural accommodation function previously performed by the natural lens. The results that can be obtained with implants of this type are variable and in any event do not constitute the subject matter of the present invention.

A third solution consists in implanting a multifocal intraocular lens that is supposed on its own to mitigate the patient's loss of accommodation, without it being necessary to have recourse to external visual equipment. The function of multifocal implants is identical to that of multifocal contact lenses, since in both cases they are aperture lenses. The multiplicity of focuses of such an implanted lens provides a depth of focus or caustic that gives the overall visual system of the patient a capacity for pseudo-accommodation. The purpose of implanting such multifocal lenses is naturally to enable the patient to avoid wearing one or more pairs of spectacles, which on the face of it appears to be advantageous. Unfortunately, such multifocal implants are often found to be a failure, either because visual acuity is insufficient, in particular for reading in the near field, or else because the pseudo-accommodation function of such implants does not operate. Under such circumstances, the implant must be replaced or the loss of acuity must be accepted without any accommodation compensation.

From this state of the art, it can be seen that compensating accommodation disorders leads to a persistent problem of intolerance or at least of difficulty in adaptation of subjects to the correcting equipments or systems that are proposed to them.

Above all, the use of multifocal aperture lenses with strong addition seeking on their own to cover the entire range of accommodation leads to the following unwelcome secondary effects:

a long period of adaptation in which the brain learns how to select the sharp image, or possible failure of such adaptation, in particular with the perception of central scotoma, double vision, or image jumping;

halos or night dazzling, associated with the spherical aberration created a portion of the light rays being unfocused; and loss of luminosity and sensitivity to contrast, associated with light rays being shared between the different focal lengths of the lens.

Nevertheless, on a daily basis, wearing aperture lenses (intraocular lenses or contact lenses) is a priori the solution that patients prefer because of its comfort and flexibility of implementation.

The use of progressive field lenses is not always satisfactory either, depending on the wearer's disorder and need for addition. The continuous progression of spherical power requires a connection, e.g. on the front face of the lens, between a far vision zone of greater radius of curvature and a near vision zone of smaller radius of curvature, and this inevitably gives rise to zones of reduced optical quality, particularly in the side portions of the lens. The disposition of these zones on the lens defines the field of sharp vision that can be used by the wearer. It is then necessary to find a compromise between field width and peripheral distortion. This is because any enlargement of the sharp field of vision implies an increase in peripheral distortion, which is troublesome in static vision and above all in dynamic vision; and conversely it is possible to limit peripheral distortion only to the detriment of the fields of view that are sharp, which become smaller. It will be understood that this problem is particularly difficult and harmful to adaptation by the wearer when the power added by the lens is considerable.

OBJECT OF THE INVENTION

The object of the present invention is to propose an alternative solution for compensating anomalies in accommodation, that is favorable both to daily comfort in use and that improves the chances of patient adaptation and tolerance, in particular when an intraocular implant is put in the place of the natural lens.

To this end, the invention provides an optical system presenting accommodation compensation, the system comprising in combination two multifocal lenses, one of them being an aperture lens and the other a field lens. The term "multifocal" is used to mean that the lens possesses a plurality of focuses that are different, depending on the zone of the lens taken into consideration.

Advantageously, the aperture lens presents power addition defined as being the difference between the maximum and minimum focal powers and the field lens presents power addition defined as being the difference between the focal powers at the reference point for far vision and or near vision, the system presenting global addition defined as being the sum of the additions of the two lenses, lying in the range 2.5 diopters to 4 diopters, and the addition of each lens is greater than or equal to one-fourth of the overall addition.

The invention thus provides a solution that makes possible and requires a reduction in the addition provided by each lens. The optical system of the invention thus shares the overall power addition required by the wearer between the field lens and the aperture lens. This results in an enlargement of the perceived fields and a reduction in distortion. This also results in smaller dependence on the diameter of the pupil, which is particularly advantageous for correcting sight in old-aged patients for whom the pupil often tends to shrink.

BRIEF DESCRIPTION OF THE DRAWINGS

Other characteristics and advantages of the invention appear on reading the following description of a particular embodiment, given by way of non-limiting example.

Reference is made to the accompanying drawings, in which.

MORE DETAILED DESCRIPTION

In the context of the present description, the following definitions are used.

The optical function of an ophthalmic lens, which gives it its correction or compensation power, is defined by its spherical, cylindrical, and prismatic refractive power properties. It will be understood that such an optical definition is of a scope that is more general than a definition purely in terms of surfaces: it defines the overall refraction effect of the lens on an incident light ray, resulting from the algebraic sum of two refractions taking place successively on the front and rear faces of the lens. This optical definition covers a plurality, or indeed an infinity, of combinations of surface pairs producing the same overall optical refraction effect, as set out in the document "Theoretical aspects of concentric varifocal lenses" by W. N. Charman, in Ophthal. Physiol. Opt. Vol. 2, No. 1, pp. 75-86, 1982, published by Pergamon Press for the British College of Ophthalmic Opticians.

In the context of the present invention, it is essentially spherical power that is of interest. The "spherical refractory power" of a lens for an incident ray passing through the lens, also referred to as the total power or the refractive power, or the mean focusing power, or the spherical power, is the magnitude that characterizes and quantifies the primary effect of spherical refringence (the "magnifying" effect) of the lens on the ray in question: if it is positive, the lens has a converging effect on the ray; if it is negative, the effect on the ray is diverging.

The numerical values for this optical magnitude as used in the definitions are obtained by the frontocofometer method of optical measurement that is well known to opticians and that is specifically described in particular in the document "Paraxial optics" by W. F. Long, in Visual Optics and Instrumentation, editor N. Charman, Macmillan Press, London 1991, pp. 418-419.

Figure 1:
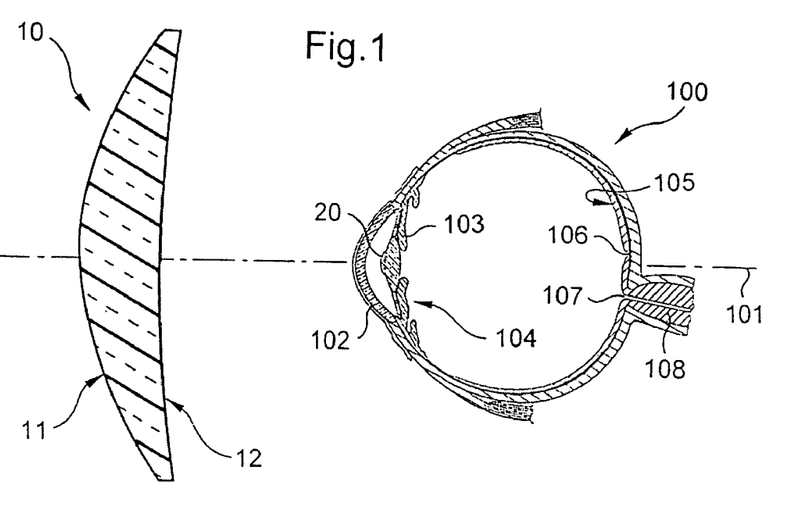
FIG. 1 is an axial section view of an optical system constituting a first embodiment of the invention.

In the first example shown in FIG. 1, there can be seen visual equipment for a patient having at least one aphakic eye 100.

The eye 100 possesses an axis 101 that may be its geometrical axis or its optical axis. Conventionally, the geometrical axis is defined as being a geometrical line passing through the eye from the anterior pole to the posterior pole and constituting an axis of revolution or of symmetry for the eyeball having a radius of 12 millimeters (mm). The optical axis is defined as being the geometrical line joining the centers of curvature of the four main interface surfaces of the eye constituted by the anterior and posterior faces of the cornea and of the natural lens (before it is removed). On the optical axis there can be found the main planes, the nodal points, and the center of rotation of the eye. It also intersects the retina between the fovea and the blind spot.

In FIG. 1, there can also be seen the main components of the eye: the cornea 102, the iris 102, the bag 104 that initially contained the lens, and at the back of the eye, the retina 105 with the fovea 106 situated above the blind spot 107 in register with the end of the optic nerve 108.

The visual equipment of the invention comprises firstly a pair of spectacles comprising two field lenses carried by a frame (not shown), and secondly an intraocular lens or a pair of intraocular lenses depending on whether one or both eyes of the patient are aphakic. When only one eye is aphakic, the equipment has a single intraocular lens for implanting in the aphakic eye in order to co-operate with the spectacles lens associated with the aphakic eye to constitute a single optical system of the invention, for correcting the aphakic eye. When both eyes are aphakic, the equipment comprises two intraocular lenses for implanting, one in each of the eyes, for co-operating with the two spectacle lenses so as to form two optical systems of the invention for correcting each of the two aphakic eyes.

Thus, the or each optical system comprises two lenses 10 and 20 in combination on the axis 101 of the eye for correction 100.

The lens 10 is mounted on the spectacle frame and is placed in registers with and at a distance from the eye 100, being a lens of the field type as defined in the introduction.

The field lens 10 is also a multifocal lens. As mentioned above, the term "multifocal" is used to mean that the lens possesses a plurality of focuses that differ depending on the zone of the lens under consideration. Specifically, the lens 10 presents progressive addition; however this option is not limiting. There are two categories of multifocal field lens: those with a power discontinuity and those with progressive addition. The field lens used in the system of the invention can belong to either of those categories.

The first category covers lenses possessing a finite number of focuses and presenting a plurality of discrete zones of differing powers that are uniform within each zone, having one or more power discontinuities. This applies typically to bifocal or trifocal lenses in which the near, intermediate, and far zones or areas are separated by lines of discontinuity that lead to a jump in the image. A lens of this type is used in the example described below with reference to FIG. 5 et seq.

The second category of multifocal field lenses is the category of lenses that are said to have progressive addition. It is this type of lens that is used in the example of FIGS. 1 and 2. In general, such a lens possesses an infinity of focuses and presents power variation that is progressive, i.e. that is continuous and monotonic. Spherical power increases in continuous manner between the top and the bottom of the lens, between a top zone for far vision and a bottom zone for near vision. The progression may be applied to the front face (convex) or to the rear face (concave), or indeed it may be shared between both faces of the lens. Such progression is obtained by continuous variation of the mean radius of curvature in one and/or the other of the two faces of the lens which becomes smaller and smaller for the front face and/or larger and larger for the rear face going towards the bottom of the lens: the progressive surface is arched on the front face and/or tapering on the rear face. Power progression may also be obtained by any other known means.

The progression of the power of the lens takes place along a line which can be straight, angled, or curved, and which is referred to as the main progression meridian which is inclined relative to the vertical in part (or completely) by a few degrees, e.g. by about 7° to 10°. The lens presents power addition that is conventionally defined as being the difference between the focal powers (i.e. spherical powers) at the reference points for far vision and for near vision.

Field progressive lenses are now well known and details of their construction and manufacture constitute the subject matter of numerous publications and commercial embodiments, in particular on the part of the Applicant. For example, it is possible to use one of the lenses sold by the Applicant under the trademarks "Varilus Comfort" and "Varilus Panamic". Reference can also be made to the descriptions of lenses given in the following documents that also stem from the Applicant:

French patent No. 2 683 642 and corresponding U.S. Pat. No. 5,270,745;
French patent No. 2 683 643 and corresponding U.S. Pat. No. 5,272,495;
French patent No. 2 699 294 and corresponding U.S. Pat. No. 5,488,442;
French patent No. 2 769 998 and corresponding U.S. Pat. No. 5,949,519;
French patent No. 2 769 999 and corresponding European patent No. 0 911 672; and
French patent No. 2 770 000 and corresponding European patent No. 0 911 670.

Figure 2:
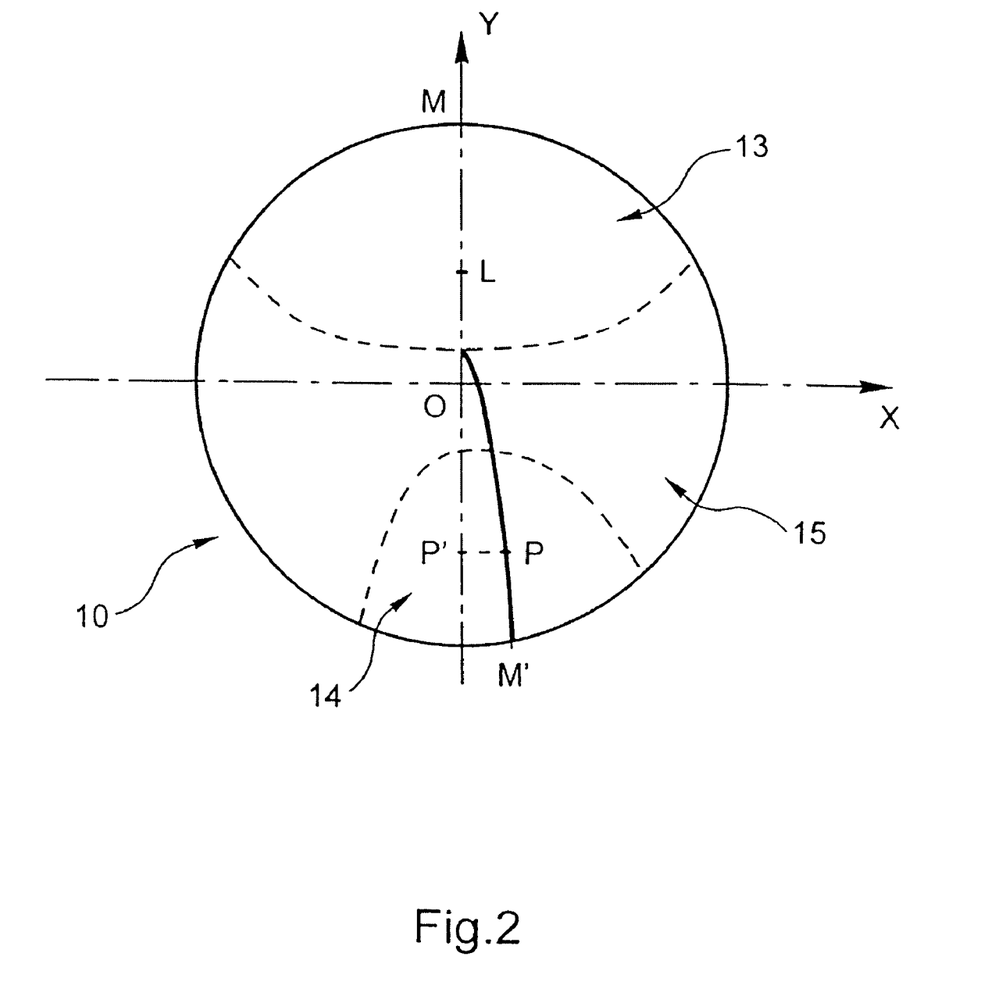
FIG. 2 is a plan view on a larger scale of the progressive field lens of FIG. 1, on its own.

In the example shown in FIGS. 1 and 2, the lens 10 thus consists in such a lens having progressive addition. It possesses a convex front face 11 that presents a complex surface carrying the power progression, and a concave rear face 12 that is spherical or toroidal and carrying the prescription.

With reference more particularly to FIG. 2, there can thus be seen on the lens 10 a far vision zone 13 situated in its top portion, a near vision zone 14 situated in its bottom portion, and an intermediate vision zone 15 situated between said two zones. It is recalled that these zones and the following definitions relate to the optical powers generated overall by the lens and result from the combination of the shapes of both faces.

In the description below, an orthonormal coordinate system is used as shown in FIG. 2. In this figure, there is a plan view of a finished lens of circular shape prior to being cut out, the lens typically presenting a diameter in the range 60 mm to 80 mm. A point of the lens is used in the prescription laboratory as the prism reference; as shown, this point is generally the geometrical center of the lens, referenced O in the figure. The prism reference point is conventionally made visible on the lens by means of a mark. The prism reference point is used by the prescription laboratory for adapting the lens to the prism prescribed for the wearer by the ophthalmologist.

The abscissa axis X corresponds to the horizontal axis of the lens and the ordinate axis Y to the vertical axis. In this definition, vertical and horizontal correspond to the orientation of the lens in use. Thus, in the progressive lenses of the Applicant, the vertical ordinate axis Y is defined by the center O of the lens (which is also the prism reference point) and by the assembly cross, both of which are marked in practice on the lens.

There can also be seen a main progression meridian MM' drawn as a bold line that passes through the three zones 13, 15, and 14 in a direction that is generally vertical, passing through a far vision reference point L, and a near vision reference point P. The main progression meridian MM' is shown in this case as being an angled line, of a shape that can advantageously vary as a function of the power addition and of the nominal spherical power at the far vision reference point L, as described by the Applicant in French patent No. 2 683 642 correspond to U.S. Pat. No. 5,270,745.

Specifically, as in lenses already sold by the Applicant, the far vision reference point L is situated on the ordinate axis Y at 8 mm above the center O of the lens, while the near vision reference point P is offset towards the nose by 3 mm from the ordinate axis Y and is projected on the ordinate axis at a point P' that is situated 14 mm below the center O. Thus, the coordinates of the point L are $X_L=0$ mm and $Y_L=8$ mm. The coordinates of the point P are $X_P=3$ mm and $Y_P=14$ mm.

Concerning its optical function, the progressive addition lens 10 is defined in particular by two main optical magnitudes: its addition and its nominal power.

Its spherical power addition $\Delta Pu_{10}$ is equal to the variation in spherical power between the reference point L of the far vision zone 13 and the reference point P of the near vision zone 14. If the power of the point P is written $Pu_{10/P}$ and the power of the point L is written $Pu_{10/L}$, then the power addition $\Delta Pu_{10}$ can be written:

$$\Delta Pu_{10}=Pu_{10/P}-Pu_{10/L}$$

The nominal power is equal to the power $Pu_{10/L}$ at the reference point L of the far vision zone.

It is shown below that in the invention the addition $\Delta Pu_{10}$ needs to satisfy certain criteria.

Since the eye 100 that is to be corrected is aphakic, the other lens 20 of the system shown in FIG. 1 is an intraocular lens for implanting in the aphakic eye 100 as a replacement for the natural lens, as shown in FIG. 1. In accordance with the definition given in the introduction, this thus constitutes an aperture lens.

In the embodiment shown, the intraocular lens 20 is implanted in the anterior chamber of the eye 100, i.e. in the portion of the eye that extends between its cornea 102 and its iris 103. Nevertheless, this particular location for implantation is not limiting: it is also possible to implant the lens in other locations using a variety of known operating techniques, and in particular it can be implanted in the posterior chamber or the capsular bag.

In order to be secured in the eye, the implant-forming lens 10 is fitted at its periphery, in diametrically opposite positions, with two generally S-shaped and elastically-deformable arms 23 suitable for bearing against the ciliary bodies of the eye 100 at the root of the iris 103.

The lens 20 is conventionally made of a synthetic material, for example of a methacrylate polymer.

The aperture lens 20 is also multifocal. As above, the term "multifocal" is used to mean that the lens possesses a plurality of focuses that differ depending on the zone of the lens under consideration. The aperture lens 20 presents power addition defined as being the difference between the maximum and minimum focal powers.

Specifically, in the example shown in FIGS. 1 to 4, the lens 20 is of the two-zone concentric bifocal type; however this option is not limiting and other types of multifocal implant could be used, as described in greater detail below.

Figure 3:
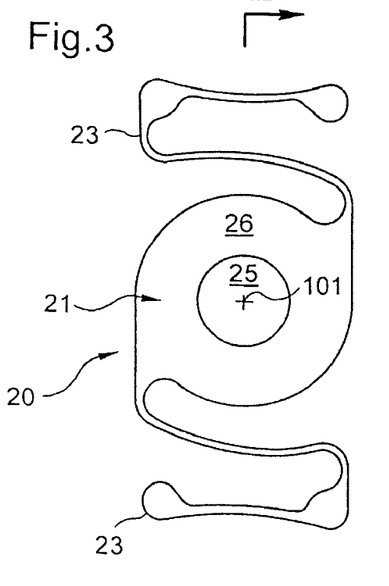
FIG. 3 is a plan view on a larger scale of the bifocal intraocular implant of FIG. 1, on its own.
Figure 4:
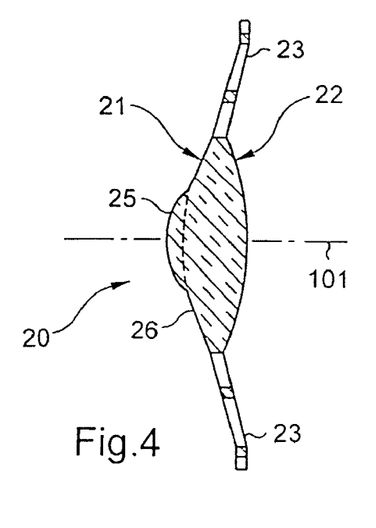
FIG. 4 is an axial section view on line III-III of FIG. 3.

With reference more particularly to FIGS. 3 and 4, the intraocular lens 20 presents an anterior face 21 and a posterior face 22. In the example shown the anterior face 21 and the posterior face 22 are convex; however other configurations could be envisaged, in particular the configuration in which the anterior face 21 is convex and the posterior face 22 is concave.

The structural and manufacturing principles concerning such multifocal intraocular lenses are nowadays well known. It suffices to recall that such a multifocal aperture lens possesses in the center of its optically useful portion a plurality of refractive or diffractive zones that differ in their focal lengths. These distinct powers thus create for each object a plurality of different images that are superposed on the retina, one of the images being sharp and the others unfocused. The operation of such a system relies on the canceling capacity of the brain, enabling it to select the image that is sharp.

In the example shown in FIGS. 2 and 3, the intraocular lens 20 is a concentric bifocal lens. It possesses a central zone 25 for near vision of power $Pu_{20/P}$ and a peripheral annular zone 26 for far vision of power $Pu_{20/L}$. The addition of the lens 20, written $\Delta Pu_{20}$, is the difference between these two powers:

$$\Delta Pu_{20} = Pu_{20/P} - Pu_{20/L}$$

According to an essential aspect of the invention, the additions $\Delta Pu_{10}$ and $\Delta Pu_{20}$ of the two lenses 10 and 20 are dependent on each other and must satisfy certain criteria.

It is considered that the optical system made up of the combination of the two lenses 10 and 20 presents overall addition defined as being the sum of the additions of the two lenses. This overall addition corresponds to within 10% to the additions prescribed for the wearer. According to the invention, it is firstly limited and secondly shared between the two lenses 10 and 20.

More precisely, this overall addition lies in the range 2.5 to 4 diopters, i.e.:

$$2.5 \text{ dpt} \leq \Delta Pu_{10} + \Delta Pu_{20} \leq 4 \text{ dpt}$$

Since the eye in question is aphakic, it may advantageously be selected to be close to 4 diopters.

Simultaneously, the addition of each of the two lenses 10 and 20 is greater than or equal to one-fourth of the overall addition, thereby guaranteeing the equilibrium and effectiveness of the sharing:

$$\Delta Pu_{10} \geq (\Delta Pu_{10} + \Delta Pu_{20})/4$$

and $$\Delta Pu_{20} \geq (\Delta Pu_{10} + \Delta Pu_{20})/4$$

Preferably, the addition is shared equally between the two lenses. Thus, in the proposed example seeking to provide overall addition of four diopters, the spectacle lens 10 and the intraocular lens 20 can both have the same addition of about 2 diopters.

FIGS. 5 to 8 show a second embodiment of the invention. This embodiment constitutes visual equipment for a patient with presbyopia. However the same equipment could equally well be used for a patient who has lost all natural accommodation power, such as an aphakic patient.

Figure 5:
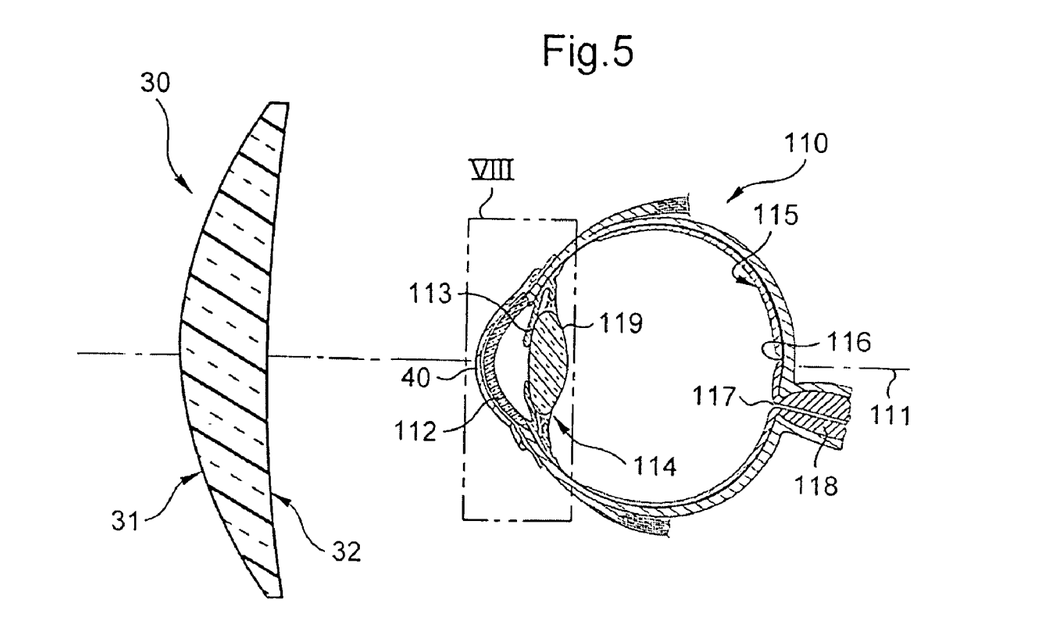
FIG. 5 is an axial section view of an optical system in a second embodiment of the invention.

The equipment comprises firstly a pair of spectacles with a lens placing facing each eye, and secondly a pair of corneal contact lenses, each positioned on a respective eye. Two optical systems of the invention are thus provided, each being constituted by a spectacle lens (field lens) and a contact lens (aperture lens) placed in register with the same eye.

In FIG. 5, there can be seen an eye 110 with its main components: cornea 112, iris 113, bag 114 containing the natural lens 119, and at the back of the eye, retina 115 with its fovea 116 situated above the blind spot 117 in register with the tip of the optic nerve 118.

Each optic system comprises two lenses 30 and 40 in combination on the axis 101 of the eye 100 to be corrected.

The lens 30 is mounted on the spectacle frame (not shown) and placed in register with and at a distance from the eye 100, being a field type lens as defined in the introduction.

The field lens 30 is also multifocal, as in the definition given above. More precisely, the lens 30 in this case belongs to the first category of multifocal field lenses defined above. It thus comprises a lens with a power discontinuity. However this option is not limiting and a lens with progressive addition could be used in combination with a contact lens.

Field lenses having a power discontinuity are well known and there is no need here to explain details of their structure and manufacture which constitute the subject matter of numerous publications and commercially available lenses. It suffices to recall that there are two main types of multifocal lens with power discontinuity, each of which is equally suitable for implementing the present invention: there are cut lenses and there are combined lenses. The multiplicity of powers for a given lens can be obtained either by changing the curvature of one of its two faces (cut or molded discontinuous multifocal lens), or by including a material having a higher refractive index (combined multifocal lens). For example, it is possible to use lenses of the kind sold by the Applicant under the trademarks "CT 28 ORMEX", "CT 28 ORMA", "TRIFOCAL 22×36", "TELEMIL", "TELEX", "TELARC".

Figure 6:
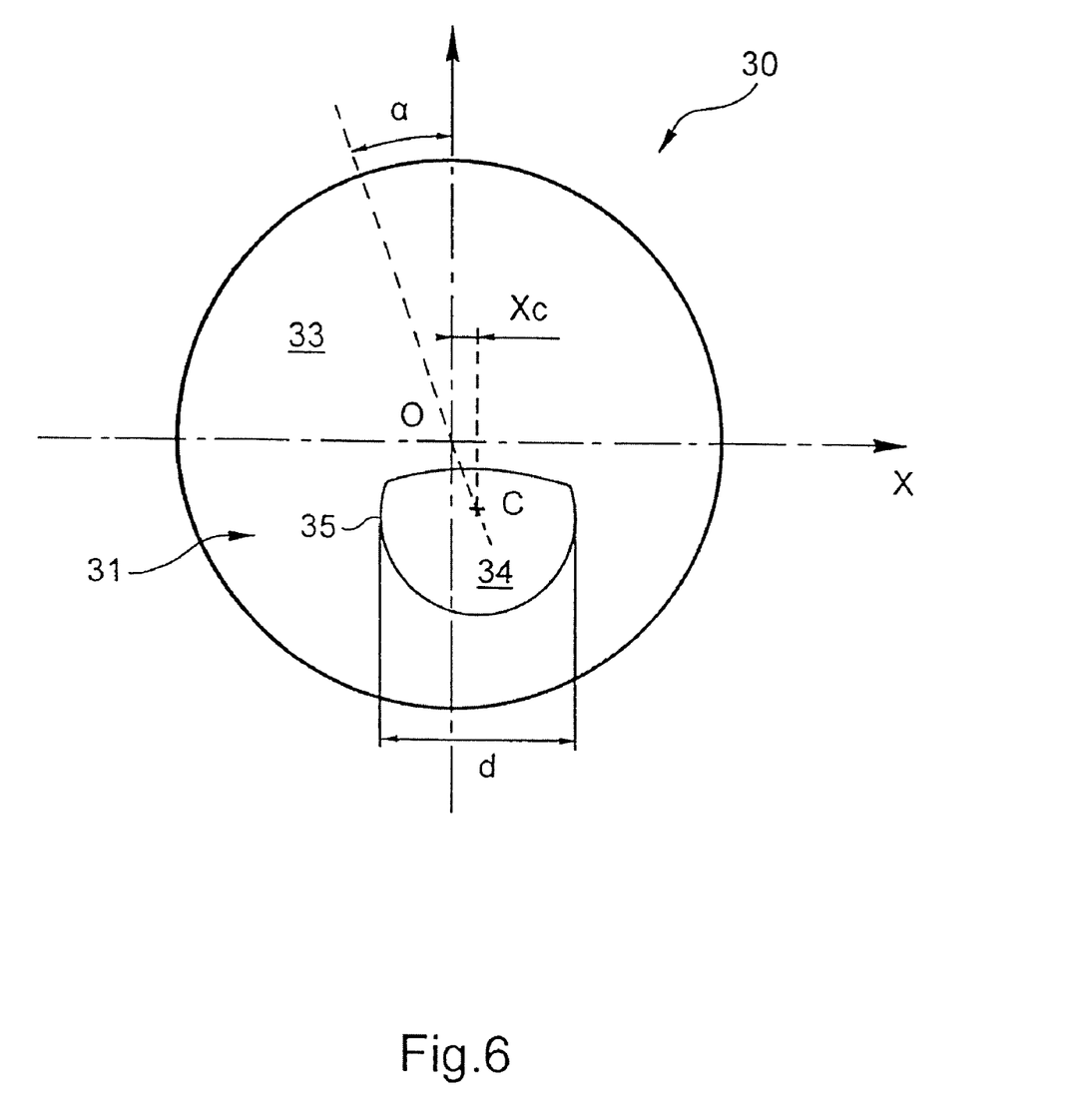
FIG. 6 is a plan view, on a larger scale, showing the bifocal field lens of FIG. 5, on its own.

In the example shown in FIGS. 5 and 6, the lens 30 thus consists in such a lens having power discontinuity. It possesses a front face 31 that is convex and that carries the power discontinuity, and a rear face 32 that is concave and spherical or toroidal, and carries the prescription.

FIG. 6 is a plan view of a finished lens whose outline, prior to being cut out, is circular in shape and typically presents a diameter of 60 mm to 80 mm. The abscissa axis X corresponding to the horizontal axis of the lens and the ordinate axis Y to the vertical axis. In this definition, vertical and horizontal correspond to the orientation of the lens when in use.

The front face 31 of the lens 30 has two spherical zones with distinct centers and curvatures. There can thus be seen a main zone 33 situated in the top portion of the lens and used for far vision. The optical center of this zone 33 coincides in this example with the geometrical center O of the lens, but it could equally well be offset by about 1 mm towards the nose along the abscissa axis X.

Within the far vision zone 33, in the bottom portion of the lens, there is a separate near vision zone 34 that is defined by a line of discontinuity 35. This zone of curvature greater than that of the zone 32 gives the lens stronger spherical power locally. The optical center of the zone 34, referenced C, is offset towards the nose by a few millimeters. Specifically, the line OC forms an angle $\alpha=10$ degrees relative to the ordinate axis Y, and the abscissa value of the center C, is Xc=3 mm. The line 35 defining the zone 34 is in the form of a portion of a circle of diameter 25 mm and of center C, being truncated on top by a generally horizontal portion which in this example is slightly curved as shown in FIG. 6 going up to a high point that is situated a few millimeters (specifically 4.5 mm) below the axis X.

Concerning its optical function, the bifocal lens 30 is defined in particular by two main optical magnitudes: its addition and its nominal power.

The spherical power addition $\Delta Pu_{30}$ is equal to the difference between the spherical powers of the far vision zone 33 and of the near vision zone 34. If the power in the far vision zone is written $Pu_{30/L}$ and the power in the near vision zone is written $Pu_{30/P}$ then:

$$\Delta Pu_{30}=Pu_{30/P}-Pu_{30/L}$$

The nominal power is equal to the power of the far vision zone $Pu_{30/L}$.

It is shown below that in the invention the addition $\Delta Pu_{30}$ must satisfy certain criteria.

The other lens 40 of the system shown in FIG. 5 is a corneal contact lens for applying against the cornea 112 of the eye 110, as shown. In accordance with the definition given in the introduction, this thus constitutes an aperture lens.

The lens 40 is a flexible lens conventionally made of a hydrophilic synthetic material, e.g.: hydroxyethyl methacrylate, acrylmonomer, (N-vinyl 2-pyrrolidone) vinylpyrrolidone, epoxy.

The contact lens 40 is also a multifocal lens. As mentioned above, the term "multifocal" is used to mean that the lens possesses a plurality of focuses that differ depending on the zone of the lens that is taken into consideration. It presents power addition that is defined as being the difference between its maximum and minimum focal powers.

The structural and manufacturing principles of such multifocal contact lenses are nowadays well known. It suffices to recall that such an aperture multifocal lens possesses, in its optically useful portions, a plurality of refractive or diffractive zones that differ in their focal lengths. These zones of distinct powers thus create for each object a plurality of different images that are superposed on the retina, one of which is sharp while the others are unfocused. The operation of such a system relies on the canceling ability of the brain enabling it to select the image that is sharp.

Figure 7:
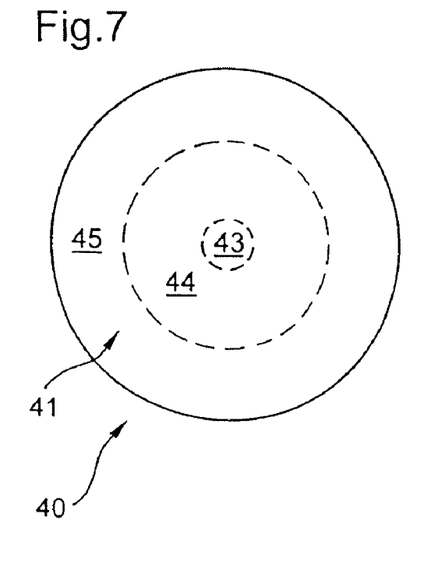
FIG. 7 is a plan view on a larger scale showing the aspherical contact lens of FIG. 5, on its own.
Figure 8:
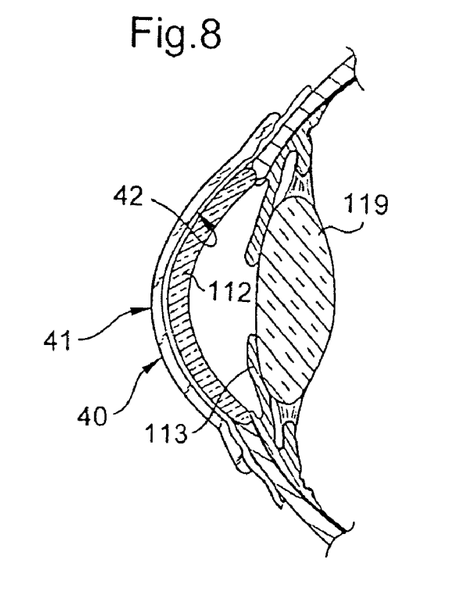
FIG. 8 is a detail view of portion VIII of FIG. 5.

Specifically, the lens 40 is of the progressive aspherical type; however this selection is not limiting, as explained in greater detail below.

The contact lens 40 possesses an anterior face 41 and a posterior face 42. The anterior face 41 is sphero-aspherical in shape, having a central zone 43 that is spherical for near vision surrounded by an annular zone of aspherical profile 44 that generates power progression going from the periphery towards the center for intermediate vision and far vision. This power progression is continuous and monotonic. The peripheral zone 45 extends the lens to provide it with a seating and retention on the eye but without performing any optical function. The central zone 43 presents a diameter of 2 mm to 4 mm while the annular zone 43 presents a diameter of 6 mm to 14 mm. The connection between the zones is continuous to the second order at least. It should be understood that the dashed-line circles defining These three zones are marked on FIG. 7 for explanatory purposes only and do not represent anything that is physically visible. The posterior face 42 is spherical or toroidal and is conventionally adapted to the prescription of the wearer.

The power of the lens in its central zone 43 for near vision is written $Pu_{40/P}$ and its power for far vision is written $Pu_{40/L}$, corresponding to the minimum power of the lens in the aspherical annular zone 44 for far vision and which is reached at the outside edge of said zone.

The addition of the lens 40, written $\Delta Pu_{40}$, is the difference between these two powers:

$$\Delta Pu_{40}=Pu_{40/P}-Pu_{40/L}$$

According to an essential aspect of the invention the additions $\Delta Pu_{30}$ and $\Delta Pu_{40}$ of the two lenses 30 and 40 depend on each other and must satisfy certain criteria.

It is considered that the optical system formed by the combination of the two lenses 30 and 40 presents overall addition defined as being the sum of the additions of the two lenses. This overall addition corresponds, to within 10%, to the additions prescribed for the wearer. According to the invention it is firstly limited and secondly shared between the two lenses 30 and 40.

More precisely, this overall addition lies in the range 2.5 diopters to 4 diopters, whence:

$$2.5 \text{ dpt} \leq \Delta Pu_{30}+\Delta Pu_{40} \leq 4 \text{ dpt}$$

Since the eye in question is not aphakic but suffers from pronounced presbyopia, the addition may advantageously be selected to be close to 3 diopters.

Simultaneously, the addition provided by each of the lenses 30 and 40 is greater than or equal to one-fourth of the overall addition, thereby guaranteeing that the distribution is balanced and effective:

$$\Delta Pu_{30} \geq (\Delta Pu_{30}+\Delta Pu_{40})/4$$

and $$\Delta Pu_{40} \geq (\Delta Pu_{30}+\Delta Pu_{40})/4$$

The distribution of addition between the two lenses is preferably equal. Thus, in the second example in which provision is made for overall addition to be 3 diopters, the spectacle lens 30 and the contact lens 40 can both present the same addition of about 1.5 diopters.

The invention is not limited to the embodiments described above. In particular, the multifocal field lens 30 may have any known shape. The examples of FIGS. 1 and 2 for the progressive lens and of FIGS. 5 and 6 for the discontinuous bifocal lens are not limiting.

Similarly, the multifocal aperture lens may have any known shape, regardless of the origin of the disorder to be corrected. The examples of FIGS. 3 and 4 for the intraocular lens and of FIGS. 7 and 8 for the contact lens are not limiting. In order to embody the invention, it is possible to use any type of multifocal aperture lens described in the prior art. In this context, it should be understood that the teaching provided for a contact lens can be transposed to use as an intraocular lens merely by adding means to the lens enabling it to be secured inside the eye.

Three categories of aperture multifocal lenses are distinguished: concentric, progressive aspherical, or diffractive. The aperture lens used in the system of the invention can belong to any one of these categories.

The first category covers lenses possessing a finite number of focuses and presenting a plurality of discrete zones having different powers which one or more power discontinuities. These are typically bifocal or trifocal lenses in which the near vision zone, the optional intermediate zone, and the far vision zone are separated by lines of discontinuity that lead to jumps in the image.

Thus, for example, it is possible to use a contact or intraocular aperture lens that is a concentric bifocal lens having two zones, of the kind described in U.S. Pat. No. 3,420,006. That is a circularly symmetrical bifocal aperture lens (specifically a contact lens, but the teaching can be transposed to an intraocular lens) possessing a central zone having power for far vision surrounded by an annular zone having power for near vision. U.S. Pat. Nos. 3,370,007, 3,726,587, and 4,636,049 describe the inverse configuration corresponding to the example of FIGS. 2 and 3 (for a contact lens) having a central zone for near vision and a peripheral annular zone for far vision.

It is also possible to use a concentric multifocal contact or intraocular lens presenting a multiplicity of zones. Such circularly symmetrical lenses possess a plurality of concentric annular zones in succession, in addition to the central portion, alternating in power between near vision power and far vision power, as described in international patent application WO 89/02251 or in U.S. Pat. No. 6,527,389. The transitions between the annuluses can be smoothed in order to present a certain amount of refractive power that is useful for intermediate vision. A third power for intermediate vision may optionally be included in the alternation.

The second category of multifocal aperture lenses that can be used is that of progressive aspherical intraocular or contact lenses. These are circularly symmetrical lenses in which power varies progressively in application of a monotonic relationship from the center towards the periphery, or vice versa. The aspherical curvature may naturally be on the anterior face or the posterior face. Although the opposite configuration could be envisaged, it is preferable for the aspherical curvature to be on the anterior face so that the near vision zone lies in the center of the lens. Various shapes are possible, and in particular: a sphero-aspherical shape with a central spherical button extended peripherally by an aspherical profile that generates the progression (or degression) in power (as in the example of FIGS. 7 and 8) or indeed an aspherical concentric shape with alternating far vision zones, near vision zone, and intermediate vision zones comprising a continuum of concentric aspherical surfaces. Examples of such progressive aperture lenses are given in British patent No. 2 288 033 and in U.S. Pat. Nos. 6,322,213, 5,214,453, 4,861,152, 4,580,882, 4,199,231, and 5,125,729.

Finally, there also exist diffractive multifocal aperture lenses. These lenses possess a diffraction grating on one of their faces. Typically they comprise a grating of concentric Fresnel lens zones. With corneal contact lenses, the diffraction grating is made on the posterior face so as to be stabilized by being immersed in tears and its depth is very shallow (about 0.003 mm) so as to avoid any harmful effect on the corneal epithelium. An example of such a lens is given in U.S. Pat. No. 4,162,122.

What is claimed is:

1. An optical system presenting accommodation compensation with a required global power addition, the system comprising in combination two multifocal lenses, one of them being an aperture lens and the other a field lens, each of them fulfilling a proper accommodation compensation function, in which the aperture lens presents a first individual power addition defined as being the difference between the maximum and minimum focal powers and the field lens presents a second individual power addition defined as being the difference between the focal powers at the reference points for far vision and near vision, the global power addition being the sum of the individual power additions of the two lenses and lying in the range 2.5 diopters to 4 diopters, and the individual addition of each lens is greater than or equal to one-fourth of the global power addition.

2. An optical system according to claim 1, in which the addition of each lens is greater than or equal to 40% of the overall addition.

3. A system according to claim 1, in which the field lens belongs to one of the following categories: a lens having progressive addition, a lens having a power discontinuity.

4. A system according to claim 1, in which the aperture lens belongs to one of the following categories: a concentric lens, a progressive aspherical lens, a diffractive lens.

5. An optical system according to claim 1, in which both lenses are of the progressive type.

6. An optical system according to claim 1, in which the eye to be corrected is aphakic, and said aperture lens is an intraocular lens for implanting the eye as a replacement for the natural lens.

7. An optical system according to claim 1, in which the aperture lens is a corneal contact lens.

8. Visual equipment for a patient having at least one aphakic eye, the equipment comprising an optical system according to claim 6 and made up firstly of a pair of spectacles possessing a lens placed in register with the eye in question and constituting said field lens of the system, and secondly of said intraocular lens.

9. Visual equipment for a patient presenting presbyopia, the equipment comprising in association with each eye, an optical system according to claim 7 and made up firstly of a pair of spectacles with a lens placed in register with each eye and constituting said field lens of the system associated with the eye, and secondly of a pair of contact lenses each placed on a respective one of the eyes and constituting said aperture lenses of the system associated with the eye.

* * * * *